(12) United States Patent
Huang et al.

(10) Patent No.: US 12,318,764 B2
(45) Date of Patent: Jun. 3, 2025

(54) COMPOSITE ZSM-5 MOLECULAR SIEVE, PREPARATION METHOD THEREFOR, CATALYST AND USE THEREOF

(71) Applicants: China Energy Investment Corporation Limited, Beijing (CN); National Institute of Clean-and-Low-Carbon Energy, Beijing (CN)

(72) Inventors: Xin Huang, Beijing (CN); Yufei Zhu, Beijing (CN); Chuanfu Wang, Beijing (CN)

(73) Assignees: China Energy Investment Corporation Limited, Beijing (CN); National Institute of Clean-and-Low-Carbon Energy, Beijing (CN)

(*) Notice: Subject to any disclaimer, the term of this patent is extended or adjusted under 35 U.S.C. 154(b) by 543 days.

(21) Appl. No.: 17/642,070

(22) PCT Filed: Apr. 10, 2020

(86) PCT No.: PCT/CN2020/084201
§ 371 (c)(1),
(2) Date: Nov. 28, 2022

(87) PCT Pub. No.: WO2021/047171
PCT Pub. Date: Mar. 18, 2021

(65) Prior Publication Data
US 2023/0132229 A1    Apr. 27, 2023

(30) Foreign Application Priority Data
Sep. 11, 2019 (CN) .......................... 201910859731.4

(51) Int. Cl.
*B01J 29/40* (2006.01)
*B01J 35/61* (2024.01)
(Continued)

(52) U.S. Cl.
CPC .............. *B01J 29/40* (2013.01); *B01J 35/615* (2024.01); *B01J 35/617* (2024.01);
(Continued)

(58) Field of Classification Search
CPC ...... B01J 29/40; B01J 37/0236; B01J 35/615; B01J 35/617; C07C 2529/40
See application file for complete search history.

(56) References Cited

U.S. PATENT DOCUMENTS 9,469,579 B2 * 10/2016 Molinier ................ B01J 19/245
2003/0190561 A1   10/2003 Kikuchi et al.
(Continued)

FOREIGN PATENT DOCUMENTS

CN          1405624 A       3/2003
CN        102616804 A       8/2012
(Continued)

OTHER PUBLICATIONS

Reda M. Mohamed, Hisham M. Aly, Mohamed F. El-Shahat, Ibrahim A. Ibrahim, Effect of the silica sources on the crystallinity of nanosized ZSM-5 zeolite, Microporous and Mesoporous Materials, vol. 79, Issues 1-3 (Year: 2005).*
(Continued)

*Primary Examiner* — Ellen M McAvoy
*Assistant Examiner* — Ming Cheung Po
(74) *Attorney, Agent, or Firm* — Calfee, Halter & Griswold LLP (57) ABSTRACT

The present disclosure discloses a composite ZSM-5 molecular sieve, a preparation method thereof, a catalyst and a use thereof.

18 Claims, 5 Drawing Sheets

(51) Int. Cl.

| | | |
|---|---|---|
| *B01J 37/00* | (2006.01) | |
| *B01J 37/02* | (2006.01) | |
| *B01J 37/03* | (2006.01) | |
| *B01J 37/04* | (2006.01) | |
| *B01J 37/08* | (2006.01) | |
| *C07C 2/86* | (2006.01) | |

(52) U.S. Cl.
CPC ......... *B01J 37/0018* (2013.01); *B01J 37/009* (2013.01); *B01J 37/0236* (2013.01); *B01J 37/031* (2013.01); *B01J 37/04* (2013.01); *B01J 37/082* (2013.01); *C07C 2/864* (2013.01); *C07C 2529/40* (2013.01)

(56) References Cited

U.S. PATENT DOCUMENTS

| | | |
|---|---|---|
| 2004/0220047 A1 | 11/2004 | Doyle et al. |
| 2007/0037693 A1 | 2/2007 | Zhu et al. |
| 2018/0345257 A1 | 12/2018 | Nubel et al. |
| 2019/0092705 A1 | 3/2019 | Liu et al. |

FOREIGN PATENT DOCUMENTS

| | | | | |
|---|---|---|---|---|
| CN | 103495436 A | | 1/2014 | |
| CN | 103936026 A | * | 7/2014 | |
| CN | 103172081 B | * | 6/2015 | |
| CN | 105621434 A | | 6/2016 | |
| CN | 105883849 A | * | 8/2016 | ............ C01B 39/40 |
| CN | 106629769 A | | 5/2017 | |
| CN | 107349954 A | | 11/2017 | |
| CN | 107792864 A | | 3/2018 | |
| CN | 107954436 A | | 4/2018 | |
| CN | 108751222 A | | 11/2018 | |
| CN | 111111748 A | | 5/2020 | |
| EP | 0970737 A2 | | 1/2000 | |
| EP | 1616616 A1 | | 1/2006 | |
| EP | 3165281 A1 | | 5/2017 | |
| JP | 2000-024515 | | 1/2000 | |
| JP | 2003292462 A | | 10/2003 | |
| JP | 2006-527068 | | 11/2006 | |
| JP | 2007-050403 | | 3/2007 | |
| WO | 2004098771 A1 | | 11/2004 | |

OTHER PUBLICATIONS

Machine Translation of CN-103172081-B (Year: 2013).*
Machine Translation of CN-105883849-A (Year: 2016).*
Machine Translation of CN-103936026-A (Year: 2014).*
Office Action from Japanese Application No. 2022-515897 dated Feb. 20, 2023 (12 pages).
Search Report and Written Opinion from Singapore Application No. 11202202386S dated Sep. 13, 2023 (9 pages).
Wang, C. et al., Maximizing sinusoidal channels of HZSM-5 for high shapeselectivity to p-xylene. Nature Communications, Sep. 25, 2019, vol. 10, pp. 4348: 1-8.
Yashima, T. et al., Selective Formation of p-Xylene by Alkylation of Toluene with Methanol on ZSM-5 type Zeolites. Studies in Surface Science and Catalysis, Dec. 31, 1981, vol. 7, pp. 739-751.
Zhang, J. et al., Increasing para-Xylene Selectivity in Making Aromatics from Methanol with a Surface-Modified Zn/P/ZSM-5 Catalyst. ACS Catalysis, Apr. 7, 2015, vol. 5, No. 5, pp. 2982-2988.

* cited by examiner

COMPOSITE ZSM-5 MOLECULAR SIEVE, PREPARATION METHOD THEREFOR, CATALYST AND USE THEREOF

CROSS REFERENCE TO RELATED APPLICATIONS

This application is a 35 USC § 371 National Stage application of International Patent Application No. PCT/CN2020/084201, which was filed Apr. 10, 2020, entitled "COMPOSITE ZSM-5 MOLECULAR SIEVE, PREPARATION METHOD THEREFOR, CATALYST AND USE THEREOF" and claims priority to Chinese Patent Application No. 201910859731.4, filed Sep. 11, 2019, which is incorporated herein by reference as if fully set forth.

FIELD

The present disclosure relates to the field of alkylation catalysts, and in particular to a composite ZSM-5 molecular sieve, a preparation method thereof, a catalyst and a use thereof.

BACKGROUND

P-xylene (PX) is an industrially important and commonly used chemical feedstock, most of p-xylene is used for the production of terephthalic acid, which is further used for producing polyester fiber and other chemical products. The demand for PX has been growing rapidly in recent years, the domestic PX demand in China is 24 million tons in 2015, but the nationwide production capacity of PX is only about 11 million tons, the market share of the imported PX has exceeding 50% in recent years. Although new PX projects have been put into operation throughout the country in recent years, the annual supply gap of PX in China is still more than 5 million tons.

Toluene alkylation reaction is one of the promising reactions with an industrial application prospect, the reaction can convert toluene into p-xylene which has high application value, and also provides an efficient route for the rational utilization of methanol. ZSM-5 molecular sieves are commonly used as catalysts in the toluene alkylation reaction. ZSM-5 molecular sieves have a group of sinusoidal pore channels and straight pore channels which are perpendicular to each other, the cross-section of each pore channel is elliptical. Wherein the sinusoidal pore channels having dimensions of 0.51 nm*0.55 nm form openings on the plane [100] of the external surface of the ZSM-5 molecular sieve, the straight pore channels having dimensions of 0.53 nm*0.56 nm form openings on the plane [010] of the external surface of the ZSM-5 molecular sieve. Theoretically, the pore channel dimensions of the ZSM-5 molecular sieve have desirable sieving function in regard to the three isomers of xylene, i.e., the dimensions of said pore channels merely allow p-xylene to pass through, while o-xylene and m-xylene are relatively difficult to pass through, thereby ensuring that the products of reaction involving with xylenes will break through the restriction of thermodynamic equilibrium and produce only p-xylene, that is, the p-xylene with a high concentration is obtained by using the shape selective and catalytic functions of the ZSM-5 molecular sieve.

However, the researchers have discovered in the experiments that the pure ZSM-5 molecular sieve cannot achieve high selectivity for xylene, there are many explanations in regard to the specific reasons, there are mainly three explanations, namely the acid sites on the external surface of the ZSM-5 molecular sieve cause isomerization of the produced p-xylene, the pore channels of said ZSM-5 molecular sieve have insufficient shape selective property, and an excessive acid strength of the ZSM-5 molecular sieve. In regard to the aforementioned reasons, many researchers have studied the method of modification by using elements such as silicon, phosphorus, magnesium, boron to reduce the acid sites on the external surface of the molecular sieve, they also discover that the strong acid content of the molecular sieve is greatly reduced, and the modifying agent partially or completely blocks the pore channels of the molecular sieve. In general, it is difficult to conclude which one of the three effects or the combination thereof jointly leads to the increased selectivity.

Despite the modification methods are effective, the methods have major problems. Firstly, in order to passivate the acid sites on the external surface of the molecular sieve, most of the modifying agents are toxic agents capable of poisoning the acid sites. Such toxic agents not only can poison the acid sites on the external surface of the molecular sieve, but also poison the acid sites in the pore channels of the molecular sieve, resulting in a decreased number of the acid sites in the pore channels of the molecular sieve. However, the acid sites in the pore channels of the molecular sieve are exactly the acid sites which can facilitate the reaction, a decreased number of the acid sites in the pore channels of the molecular sieve necessarily signifies the reduced activity of the molecular sieve. Secondly, while the pore size is decreased by the modifying agents, the presence of said modifying agents will inevitably result in the circumstance of blocking the pore channels, it decreases the pore volume of the molecular sieve, hinders the access of reactants to and from the molecular sieve, thereby decreasing activity of the molecular sieve. Thirdly, the modifying agents, being exotic, are unstable in the molecular sieve skeleton, they will gradually run off along with an elapse of the reaction time, resulting in a decreased shape-selective property of the molecular sieve, and the modifying agents are prone to deposit in the chemical conduits behind the reactor, thereby causing blockage of the conduits.

On the other hand, with respect to the two groups of pore channels of the ZSM-5 molecular sieve, the sinusoidal pore channels are smaller and more tortuous than the straight pore channels, thus have better shape-selective effect for p-xylene. However, it is impossible that the ZSM-5 molecular sieve merely comprises the sinusoidal pore channels.

Therefore, it is urgently required to develop a novel ZSM-5 molecular sieve that can improve selectivity of p-xylene in the alkylation reaction of toluene methanol.

SUMMARY

The present disclosure provides a composite ZSM-5 molecular sieve, a preparation method thereof, a catalyst and a use thereof, in order to overcome the problems in the prior art that it is difficult to obtain a desired shape-selective and catalytic functions by modifying the ZSM-5 molecular sieve, the selectivity to xylene is not high when the ZSM-5 molecular sieve is used in the alkylation reaction of toluene methanol.

In order to fulfill the above purpose, a first aspect of the present disclosure provides a composite ZSM-5 molecular sieve whose single crystal comprises a main crystal and a twin crystal; wherein the main crystal and the twin crystal are both ZSM-5 crystals; a crystal plane [010] of the main crystal is covered by a crystal plane [100] of the twin crystal; the ratio of the number of sinusoidal pore openings (zigzag pore openings) to the number of straight pore openings on the external surface of the single crystal of the composite ZSM-5 molecular sieve is (0.7-10:1); the molar ratio $Y_1$ of Si element to Al element within 10 nm of the surface of the composite ZSM-5 molecular sieve is (300-2,000):1.

In a second aspect, the present disclosure provides a method for preparing a composite ZSM-5 molecular sieve comprising:
(1) mixing a silicon source and an aluminum source in the presence of water, a first templating agent and a second templating agent, adjusting the pH to be within a range of 11-13.5, and then performing crystallization;
(2) subjecting the crystallized product to a solid-liquid separation, and calcining the obtained solid phase to prepare the composite ZSM-5 molecular sieve;
wherein the first templating agent is at least one selected from the group consisting of tetraethylammonium hydroxide, tetrapropylammonium hydroxide, tetrapropylammonium bromide and tetrabutylammonium hydroxide, the second templating agent is at least one selected from the group consisting of ethylenediamine, n-butylamine, hexamethylenediamine, ethylamine, ethanol and ethanolamine; and the used amount of the first templating agent to the second templating agent in a molar ratio is 1:(1-30).

In a third aspect, the present disclosure provides a composite ZSM-5 molecular sieve produced with the preparation method thereof.

In a fourth aspect, the present disclosure provides a catalyst comprising the composite ZSM-5 molecular sieve of the present disclosure.

In a fifth aspect, the present disclosure provides a use of the composite ZSM-5 molecular sieve thereof or the catalyst provided by the present disclosure in the alkylation reaction of toluene methanol to prepare p-xylene.

Due to the above technical scheme, the single crystal of the composite ZSM-5 molecular sieve provided by the present disclosure has a large ratio of the number of sinusoidal pore openings to the number of straight pore openings, and during the reaction process for preparing p-xylene, all the xylene molecules must diffuse outward via the sinusoidal pore channels of the molecular sieve, thereby greatly improving the resistance to the diffusion of xylene molecules and the shape-selective property of the molecular sieve for p-xylene. Moreover, in light of the high molar ratio of Si element to Al element on the surface of the composite ZSM-5 molecular sieve, the externally added modifying agent is not required, so as to avoid a circumstance that the running off of said modifying agent causes a reduced selectivity of p-xylene, thus the stability of the molecular sieve is greatly improved.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

Figure 1:
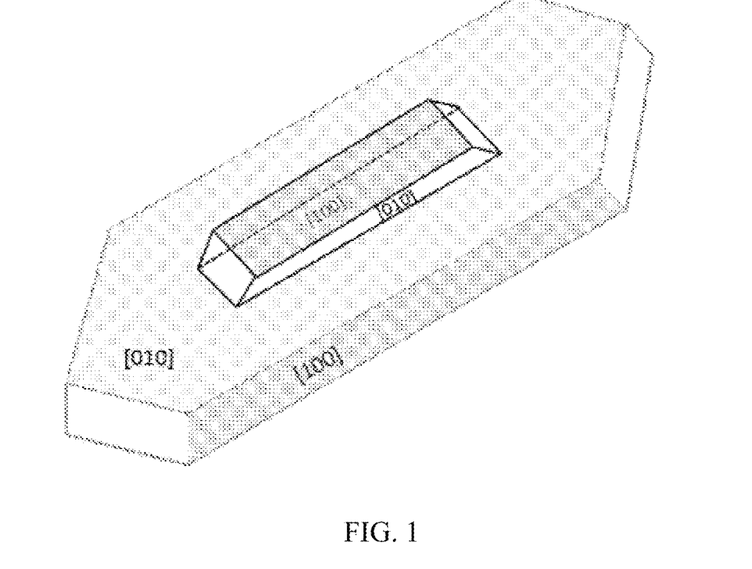
FIG. 1 illustrates a schematic diagram of a single crystal of the composite ZSM-5 molecular sieve in the present disclosure.

In a first aspect, the present disclosure provides a composite ZSM-5 molecular sieve, as shown in FIG. 1, whose a single crystal comprises a main crystal and a twin crystal; wherein the main crystal and the twin crystal are ZSM-5 crystals; the twin crystal and the main crystal grow in the superimposed manner at an angle of 90°, such that a crystal plane [010] of the main crystal is covered by a crystal plane [100] of the twin crystal. In the present disclosure, both crystal planes [010] of the main crystal are covered by a crystal plane [100] of the twin crystal. The ratio of the number of sinusoidal pore openings to the number of straight pore openings on the external surface of the single crystal of the composite ZSM-5 molecular sieve is (0.7-10:1); the molar ratio (hereinafter referred to as $Y_1$) of Si element to Al element within 10 nm of the surface of the composite ZSM-5 molecular sieve is (300-2,000):1.

According to parameters published by the International Zeolite Association (IZA), there is a straight pore opening for each area of 20.090 angstrom×13.142 angstrom on a crystal plane [010] of the ZSM-5 molecular sieve, and there is a sinusoidal pore opening for each area of 19.7380 angstrom×13.1420 angstrom. The dimensions of each crystal plane of each molecular sieve crystal are obtained by the SEM spectrogram, and the ratio of the number of sinusoidal pore openings to the number of straight pore openings on the external surface of the single crystal of the composite ZSM-5 molecular sieve according to the present disclosure is obtained by calculating an area of the crystal plane. Preferably, the ratio of the number of sinusoidal pore openings to the number of straight pore openings on the external surface of the single crystal of the composite ZSM-5 molecular sieve is (0.9-3.2):1.

Figure 2:
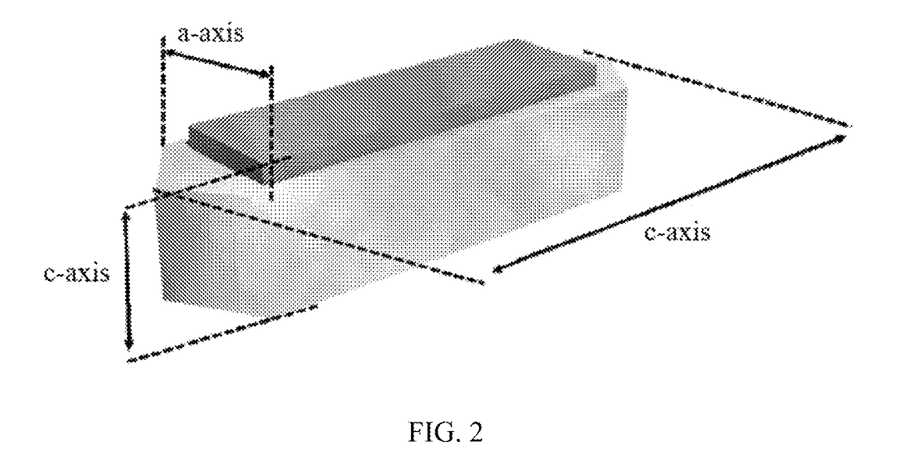
FIG. 2 illustrates a schematic diagram of the three dimensional stereostructure of a single crystal of the composite ZSM-5 molecular sieve in the present disclosure.

According to the present disclosure, it is preferred that a single crystal of the composite ZSM-5 molecular sieve has a length of 10-50 μm, a height of 1-20 μm and a width of 1-20 μm; and a single crystal of the composite ZSM-5 molecular sieve has a specific surface area of 200-600 m²/g. As shown in FIG. 2 of the present disclosure, the length refers to the maximum distance at both ends of a single crystal of the composite ZSM-5 molecular sieve in the c-axis direction, the height refers to the maximum distance at both ends of a single crystal of the composite ZSM-5 molecular sieve in the b-axis direction, and the width refers to the maximum distance at both ends of a single crystal of the composite ZSM-5 molecular sieve in the a-axis direction.

In the present disclosure, the content of Si element and Al element within 10 nm of the surface of the composite ZSM-5 molecular sieve is scanned by using the X-ray Photoelectron Spectroscopy (XPS) technique, and the molar ratio $Y_1$ is obtained by calculating. $Y_1$ is preferably (300-1,500):1, more preferably (500-1,200):1. In the present disclosure, within 10 nm of the surface of the composite ZSM-5 molecular sieve refers to the portion having a thickness within 10 nm from the surface of the composite ZSM-5 molecular sieve.

According to the present disclosure, the molar ratio (hereinafter referred to $Y_2$) of Si element to Al element of the composite ZSM-5 molecular sieve as a whole is preferably (20-600):1, more preferably (50-300):1. After exposing the inside of the molecular sieve by crushing the particles of the composite ZSM-5 molecular sieve, the contents of Si element and Al element of the composite ZSM-5 molecular sieve as a whole are calculated by using the XPS technique, the molar ratio $Y_2$ is obtained by calculating.

The composite ZSM-5 molecular sieve provided by the present disclosure is aluminum-poor on the surface and aluminum-rich on the inside; when the composite ZSM-5 molecular sieve is used for preparing p-xylene, the generated p-xylene will not be isomerized on the surface of the composite ZSM-5 molecular sieve, such that the p-xylene selectivity can be improved.

In a second aspect, the present disclosure provides a method for preparing a composite ZSM-5 molecular sieve comprising:
(1) mixing a silicon source and an aluminum source in the presence of water, a first templating agent and a second templating agent, adjusting the pH to be within a range of 11-13.5, and then performing crystallization;
(2) subjecting the crystallized product to a solid-liquid separation, and calcining the obtained solid phase to prepare the composite ZSM-5 molecular sieve;
wherein the first templating agent is at least one selected from the group consisting of tetraethylammonium hydroxide, tetrapropylammonium hydroxide, tetrapropylammonium bromide and tetrabutylammonium hydroxide, the second templating agent is at least one selected from the group consisting of ethylenediamine, n-butylamine, hexamethylenediamine, ethylamine, ethanol and ethanolamine; and the used amount of the first templating agent to the second templating agent in a molar ratio is 1:(1-30).

The inventors of the present disclosure have discovered in researches that by selecting the specific kinds of the first templating agent and the second templating agent, and controlling a ratio of the used amount of the first templating agent to the second templating agent within a certain range, the composite ZSM-5 molecular sieve crystals comprising a main crystal and a twin crystal can be obtained, and a crystal plane [010] of the main crystal is covered by a crystal plane [100] of the twin crystal, such that the ratio of the number of sinusoidal pore openings to the number of straight pore openings on the external surface of the single crystal of the composite ZSM-5 molecular sieve is high, and the molar ratio of Si element to Al element within 10 nm of the surface of the composite ZSM-5 molecular sieve is large. A molar ratio of the used amount of the first templating agent to the second templating agent is preferably 1:(3-20), more preferably 1:(5-15).

Preferably, the pH in step (1) is adjusted to 11.2-13. The inventors of the present disclosure have discovered in researches that by controlling pH to be within the above range, the obtained composite ZSM-5 molecular sieve can further improve the p-xylene selectivity when it is used in a reaction for producing para-xylene.

In the present disclosure, the pH may be adjusted by means of the existing technical means, such as adjusting the pH by adding an alkaline substance, the alkaline substance is preferably sodium hydroxide and/or potassium hydroxide.

In the present disclosure, the silicon source may be at least one selected from the group consisting of an organic silicone grease, a silica sol and a solid silica gel. The organic silicone grease is preferably ethyl orthosilicate and/or methyl orthosilicate. The aluminum source may be at least one selected from the group consisting of sodium metaaluminate, sodium aluminate, aluminum nitrate, aluminum sulfate and aluminum isopropoxide.

Preferably, a molar ratio of the used amount of the silicon source, the aluminum source, the first templating agent, the second templating agent and water is 100:(0.08-2.5):(0.5-6):(0.5-60):(100-4,000); wherein the silicon source is calculated in terms of $SiO_2$, the aluminum source is calculated in terms of $Al_2O_3$. Further preferably, the silicon source, the aluminum source, the first templating agent, the second templating agent and water are used in a molar ratio of 100:(0.4-2):(1-6):(3-30):(500-4,000). In the present disclosure, the used amount of water refers to the amount of water in the overall system, when the silicon source, the aluminum source, the first templating agent or the second templating agent are added in the form of an aqueous solution, the used amount of water comprises the solvent water in the aqueous solution.

The conditions for carrying out the crystallization in step (1) are not particularly defined in the present disclosure, in order to produce a favorable crystallization effect. The crystallization conditions in step (1) preferably comprise a temperature of 120-250° C. and a time of 12-72 h, more preferably a temperature of 150-180° C. and a time of 24-60 h.

The conditions for carrying out the calcination in step (2) are not particularly defined in the present disclosure, in order to produce a favorable calcination effect. The calcination conditions preferably comprise a temperature of 500-700° C., and a time of 1-24 h, more preferably 4-12 h.

According to a preferred embodiment of the present disclosure, the solid phase obtained from the solid-liquid separation is subjected to drying prior to calcining.

Preferably, the drying conditions preferably comprise a temperature of 90-200° C. and a time of 2-12 h.

In a third aspect, the present disclosure provides a composite ZSM-5 molecular sieve produced with the preparation method of the present disclosure.

Wherein a single crystal of the composite ZSM-5 molecular sieve comprises a main crystal and a twin crystal; wherein the main crystal and the twin crystal are both ZSM-5 crystals; a crystal plane [010] of the main crystal is covered by a crystal plane [100] of the twin crystal; the ratio of the number of sinusoidal pore openings to the number of straight pore openings on the external surface of the single crystal of the composite ZSM-5 molecular sieve is (0.7-10:1); the molar ratio $Y_1$ of Si element to Al element within 10 nm of the surface of the composite ZSM-5 molecular sieve is (300-2,000):1.

Preferably, the ratio of the number of sinusoidal pore openings to the number of straight pore openings on the external surface of the single crystal of the composite ZSM-5 molecular sieve is (0.9-3.2):1.

Preferably, the molar ratio $Y_1$ of Si element to Al element within 10 nm of the surface of the composite ZSM-5 molecular sieve is (500-1,200):1.

Preferably, the molar ratio $Y_2$ of Si element to Al element of the composite ZSM-5 molecular sieve as a whole is (20-600):1, preferably (50-300):1.

In a fourth aspect, the present disclosure provides a catalyst comprising the composite ZSM-5 molecular sieve of the present disclosure. According to the present disclosure, the catalyst comprises the composite ZSM-5 molecular sieve as an active component. Besides the composite ZSM-5 molecular sieve, the catalyst may further comprise the conventional catalyst ingredients such as a modifying agent, a pore-enlarging agent and a binder, and may have a conventional structure and shape of the catalysts in the art, such that the catalysts are applicable to the different types of reactors. The content of said composite ZSM-5 molecular sieve may be 40-90 wt % of the total amount of the catalyst.

In a fifth aspect, the present disclosure provides a use of the composite ZSM-5 molecular sieve of the present disclosure or the catalyst of the present disclosure in the alkylation reaction of toluene methanol to prepare p-xylene.

According to the present disclosure, the catalyst and the composite ZSM-5 molecular sieve have substantially equivalent catalytic effect to the alkylation reaction of toluene methanol for preparing p-xylene.

When compared with the conventionally modified ZSM-5 molecular sieves, the composite ZSM-5 molecular sieve provided by the present disclosure has the following advantages:

(1) The composite ZSM-5 molecular sieve of the present disclosure utilizes the sinusoidal pore channels having a large diffusion resistance to the xylene molecules to accomplish the shape-selective function of said molecular sieve to a large extent, prevents the straight pore channels having poor shape-selective effect from participating the shape-selective and catalytic process, such that the selectivity of said molecular sieve in regard to p-xylene can be greatly improved.

(2) In contrast to the modified ZSM-5 molecular sieve, the composite ZSM-5 molecular sieve of the present disclosure is synthesized and prepared directly by a one-step process, there is not a process of modifying the molecular sieve, thus the number of acid centers is not affected by the modification process, and the original activity of the molecular sieve is retained by 100%. In addition, there is not the circumstance with respect to running off of the modifying agent and degraded shape-selective property of the molecular sieve during the reaction process.

(3) The molecular sieve obtained by the present disclosure is aluminum-poor on the external surface, when the molecular sieve is used for the catalytic production of p-xylene, the generated p-xylene is not isomerized on a surface of the composite ZSM-5 molecular sieve, such that its p-xylene selectivity can be further improved.

The present disclosure will be described below in detail with reference to examples. In the following examples, the SEM spectrograms were measured by the spherical-aberration correction scanning electron microscopy (ac-SEM) (Nova NanoSEM 450, commercially available from FEI).

According to parameters published by the International Zeolite Association (IZA), there was a straight pore opening for each area of 20.090 angstrom×13.142 angstrom on a crystal plane [010] of the ZSM-5 molecular sieve, and there was a sinusoidal pore opening for each area of 19.7380 angstrom×13.1420 angstrom. The dimensions of each crystal plane of each molecular sieve crystal were obtained by the SEM spectrogram, and the ratio of the number of sinusoidal pore openings to the number of straight pore openings on the external surface of the single crystal of the composite ZSM-5 molecular sieve according to the present disclosure was obtained by calculating an area of the crystal plane.

The Elemental analysis of the composite ZSM-5 molecular sieve was performed by using the X-ray photoelectron spectroscopy (ESCALAB 250Xi, commercially available from Thermo-Fisher).

1) The molar ratio $Y_1$ was obtained by scanning the elements within 10 nm of the surface of the composite ZSM-5 molecular sieve by using the X-ray Photoelectron Spectroscopy (XPS) technique;

2) After exposing the inside of the molecular sieve by crushing the particles of the composite ZSM-5 molecular sieve, the molar ratio $Y_2$ was obtained by using the X-ray Photoelectron Spectroscopy (XPS) technique.

The length, height and width of a single crystal of the composite ZSM-5 molecular sieve were obtained by the spherical-aberration correction scanning electron microscopy (ac-SEM); the specific surface area was measured by $N_2$ physical adsorption after pretreatment of the test sample at 350° C., and the specific surface area was calculated by using the Brunauer, Emmett and Teller (BET) model.

Example 1

(1) 60 g of silica sol solution (30 wt %) was mixed with sodium metaaluminate, tetrapropylammonium bromide, n-butylamine and water, wherein the used amounts of said raw materials satisfied $SiO_2:Al_2O_3$:tetrapropylammonium bromide:n-butylamine:water=100:0.67:4.5:35.3:3,333 (molar ratio), sodium hydroxide was added to adjust the pH to 12, then stirred uniformly for 30 minutes, the mixture was poured into a rotary self-pressurization crystallization kettle to carry out crystallization at 180° C. for 48 h;

(2) the crystallized sample of step (1) was filtered and washed with deionized water to neutral, then placed in an oven for drying at 120° C. for 2 h; the dried solid was placed in a muffle furnace, the temperature was raised from room temperature (25° C.) to 550° C. at a temperature rise rate of 1° C./min under a flowing air atmosphere, the dried solid was then roasted at a constant temperature of 550° C. for 5 h, and subsequently cooled naturally to room temperature to prepare the composite ZSM-5 molecular sieve M1. The composite ZSM-5 molecular sieve had a length of 50 μm, a height of 20 μm, a width of 20 μm, and a specific surface area of 420 $m^2/g$.

Figure 3:
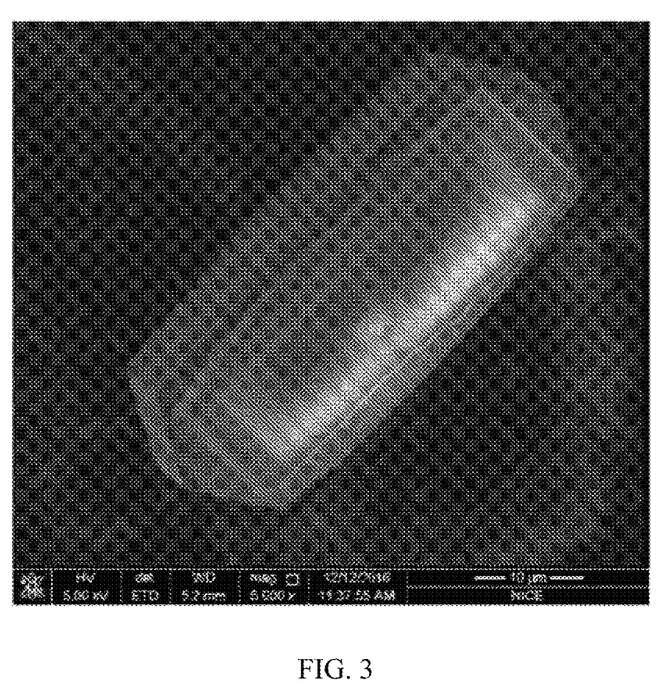
FIG. 3 illustrates a SEM diagram of a single crystal of the composite ZSM-5 molecular sieve in the present disclosure.

As characterized by the SEM spectrogram (as shown in FIG. 3), approximately 20% of the area of a crystal plane [010] of the main crystal of a single crystal of the composite ZSM-5 molecular sieve M1 was covered by the twin crystal which grew at an angle of 90° relative to the body. The ratio of the number of sinusoidal pore openings to the number of straight pore openings on the external surface of the composite ZSM-5 molecular sieve was illustrated in Table 1.

Figure 4:
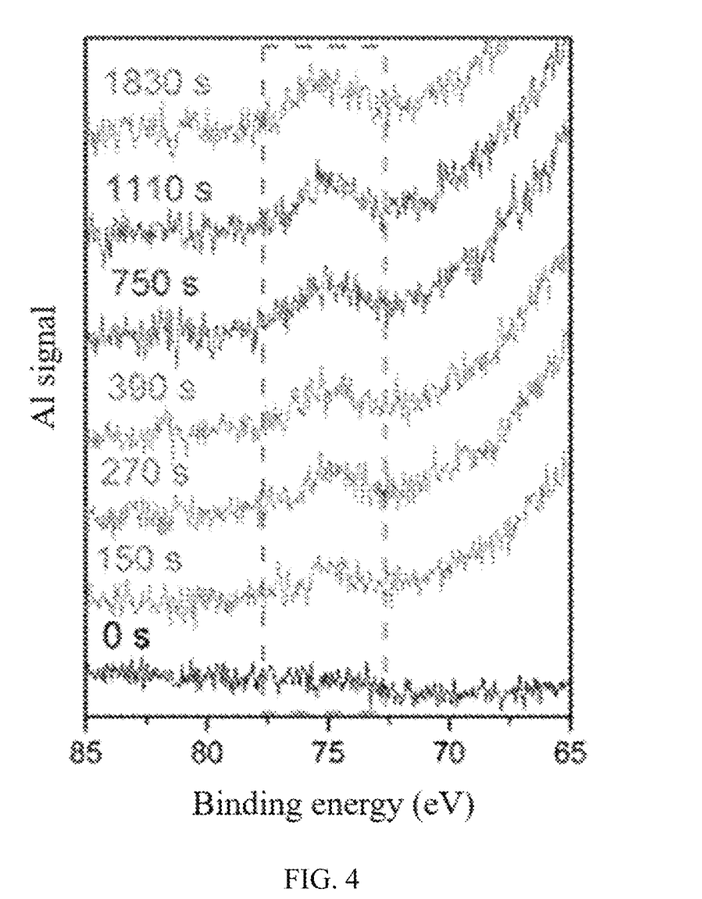
FIG. 4 illustrates an XPS Al signal spectrogram of the composite ZSM-5 molecular sieve obtained by the present disclosure under the different etching time conditions.
Figure 5:
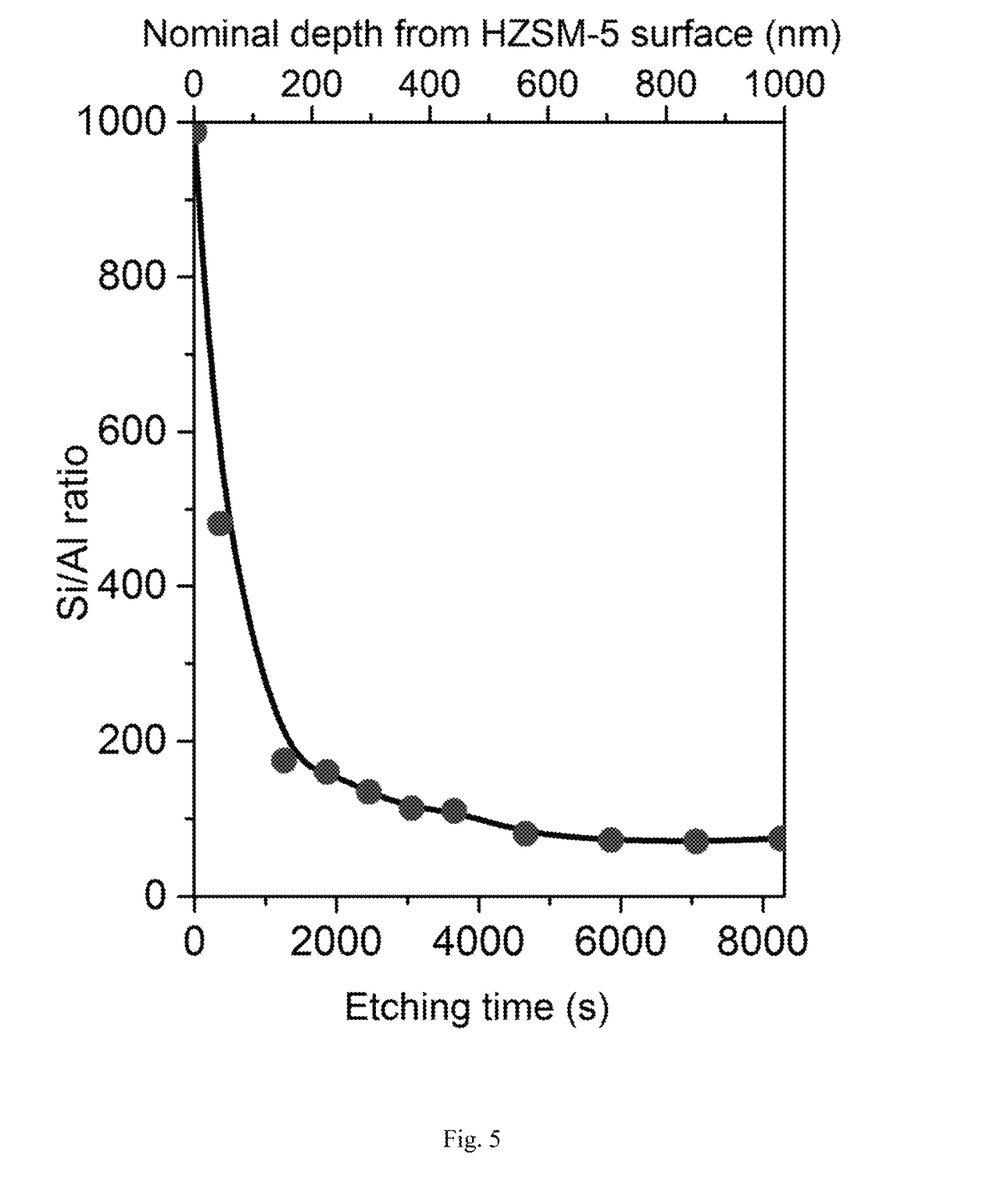
FIG. 5 illustrates the XPS Si/Al values of the composite ZSM-5 molecular sieve obtained by the present disclosure under the different etching conditions.

The composite ZSM-5 molecular sieve was subjected to the elemental analysis, the results were shown in FIG. 4. As can be seen from FIG. 4, the signal value of the aluminum element was continuously increased along with an increase of the ion etching depth. The Si/Al molar ratio under different etching time conditions was calculated, as shown in FIG. 5. As illustrated in FIG. 5, the Si/Al molar ratio in the composite ZSM-5 molecular sieve became progressively smaller along the direction from a surface of the molecular sieve to the inside, indicating that the composite ZSM-5 molecular sieve was aluminum-poor on the surface and aluminum-rich on the inside. The values of $Y_1$ and $Y_2$ of the composite ZSM-5 molecular sieve were shown in Table 1.

Example 2

(1) 18 g of solid silica gel powder (with a silica content more than 99 wt %) was mixed with aluminum sulfate, aqueous solution of tetrapropylammonium hydroxide (25 wt %), hexamethylenediamine and water, wherein the used amounts of said raw materials satisfied $SiO_2$:$Al_2O_3$:tetrapropylammonium hydroxide:hexamethylenediamine:water=100:0.67:3:30:3,000 (molar ratio), potassium hydroxide was added to adjust the pH to 12.5, then stirred uniformly for 30 minutes, the mixture was poured into a rotary self-pressurization crystallization kettle to carry out crystallization at 180° C. for 48 h;

(2) the crystallized sample of step (1) was filtered and washed with deionized water to neutral, then placed in an oven for drying at 150° C. for 2 h; the dried solid was placed in a muffle furnace, the temperature was raised from room temperature (25° C.) to 550° C. at a temperature rise rate of 2° C./min under a flowing air atmosphere, the dried solid was then roasted at a constant temperature of 550° C. for 12 h, and subsequently cooled naturally to room temperature to prepare the composite ZSM-5 molecular sieve M2. The composite ZSM-5 molecular sieve had a length of 40 μm, a height of 15 μm, a width of 14 μm, and a specific surface area of 340 m²/g.

The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Example 3

(1) 62.4 g of ethyl orthosilicate was mixed with aluminum sulfate, aqueous solution of tetrapropylammonium hydroxide (25 wt %), ethylenediamine and water, wherein the used amounts of said raw materials satisfied $SiO_2$:$Al_2O_3$:tetrapropylammonium hydroxide:ethylenediamine:water=100:0.8:4:36:2,000 (molar ratio), potassium hydroxide was added to adjust the pH to 13, then stirred uniformly for 30 min, the mixture was poured into a rotary self-pressurization crystallization kettle to carry out crystallization at 150° C. for 60 h;

(2) the crystallized sample of step (1) was filtered and washed with deionized water to neutral, then placed in an oven for drying at 150° C. for 2 h; the dried solid was placed in a muffle furnace, the temperature was raised from room temperature (25° C.) to 550° C. at a temperature rise rate of 5° C./min under a flowing air atmosphere, the dried solid was then roasted at a constant temperature of 550° C. for 12 h, and subsequently cooled naturally to room temperature to prepare the composite ZSM-5 molecular sieve M3. The composite ZSM-5 molecular sieve had a length of 33 μm, a height of 12 μm, a width of 15 μm, and a specific surface area of 300 m²/g.

The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Example 4

(1) 18 g of solid silica gel powder (with a silica content more than 99 wt %) was mixed with sodium metaaluminate, tetrapropylammonium bromide, ethanolamine and water, wherein the used amounts of said raw materials satisfied $SiO_2$:$Al_2O_3$:tetrapropylammonium bromide:ethanolamine:water=100:0.7:5:60:1,000 (molar ratio), sodium hydroxide was added to adjust the pH to 12.5, then stirred uniformly for 30 minutes, the mixture was poured into a rotary self-pressurization crystallization kettle to carry out crystallization at 170° C. for 24 h;

(2) the crystallized sample of step (1) was filtered and washed with deionized water to neutral, then placed in an oven for drying at 120° C. for 2 h; the dried solid was placed in a muffle furnace, the temperature was raised from room temperature (25° C.) to 550° C. at a temperature rise rate of 5° C./min under a flowing air atmosphere, the dried solid was then roasted at a constant temperature of 550° C. for 5 h, and subsequently cooled naturally to room temperature to prepare the composite ZSM-5 molecular sieve M4. The composite ZSM-5 molecular sieve had a length of 16 μm, a height of 5 μm, a width of 8 μm, and a specific surface area of 314 m²/g.

The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Example 5

(1) 60 g of a silica sol solution (30 wt %) was mixed with sodium metaaluminate, aqueous solution of tetraethylammonium hydroxide (25 wt %), ethylamine and water, wherein the used amounts of said raw materials satisfied $SiO_2$:$Al_2O_3$:tetraethylammonium hydroxide:ethylamine:water=100:0.8:3:45:4,000 (molar ratio), sodium hydroxide was added to adjust the pH to 11.6, then stirred uniformly for 30 minutes, the mixture was poured into a rotary self-pressurization crystallization kettle to carry out crystallization at 170° C. for 24 h;

(2) the crystallized sample of step (1) was filtered and washed with deionized water to neutral, then placed in an oven for drying at 120° C. for 2 h; the dried solid was placed in a muffle furnace, the temperature was raised from room temperature (25° C.) to 550° C. at a temperature rise rate of 5° C./min under a flowing air atmosphere, the dried solid was then roasted at a constant temperature of 550° C. for 5 h, and subsequently cooled naturally to room temperature to prepare the composite ZSM-5 molecular sieve M5. The composite ZSM-5 molecular sieve had a length of 27 μm, a height of 14 μm, a width of 10 μm, and a specific surface area of 354 m²/g.

The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Example 6

(1) 18 g of solid silica gel powder (with a silica content more than 99 wt %) was mixed with sodium metaaluminate, aqueous solution of tetrabutylammonium hydroxide (25 wt %), ethylamine and water, wherein the used amounts of said raw materials satisfied $SiO_2$:$Al_2O_3$:tetrabutylammonium hydroxide:ethanol:water=100:0.6:2:40:3,000 (molar ratio), sodium hydroxide was added to adjust the pH to 13, then stirred uniformly for 30 minutes, the mixture was poured into a rotary self-pressurization crystallization kettle to carry out crystallization at 170° C. for 24 h;

(2) the crystallized sample of step (1) was filtered and washed with deionized water to neutral, then placed in an oven for drying at 120° C. for 2 h; the dried solid was placed in a muffle furnace, the temperature was raised from room temperature (25° C.) to 550° C. at a temperature rise rate of 5° C./min under a flowing air atmosphere, the dried solid was then roasted at a constant temperature of 550° C. for 5 h, and subsequently cooled naturally to room temperature to prepare the composite ZSM-5 molecular sieve M6. The composite ZSM-5 molecular sieve had a length of 10 μm, a height of 4 μm, a width of 4 μm, and a specific surface area of 370 $m^2/g$.

The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Example 7

The molecular sieve was prepared according to the method of Example 1, except that the used amounts of said raw materials satisfied $SiO_2$:$Al_2O_3$:tetrapropylammonium bromide:n-butylamine:water=100:0.67:2:60:3,333 (molar ratio), so as to prepare a composite ZSM-5 molecular sieve M7. The composite ZSM-5 molecular sieve had a length of 30 μm, a height of 13 μm, a width of 13 μm, and a specific surface area of 300 $m^2/g$.

The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Example 8

The molecular sieve was prepared according to the method of Example 1, except that the used amounts of said raw materials satisfied $SiO_2$:$Al_2O_3$:tetrapropylammonium bromide:n-butylamine:water=100:0.67:2:6:3,333 (molar ratio), so as to prepare a composite ZSM-5 molecular sieve M8. The composite ZSM-5 molecular sieve had a length of 10 μm, a height of 2 μm, a width of 3 μm, and a specific surface area of 410 $m^2/g$.

The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Example 9

The molecular sieve was prepared according to the method of Example 2, except that the pH was adjusted to 11 to prepare a composite ZSM-5 molecular sieve M9. The composite ZSM-5 molecular sieve had a length of 40 μm, a height of 20 μm, a width of 15 μm, and a specific surface area of 320 $m^2/g$.

The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Example 10

The molecular sieve was prepared according to the method of Example 1, except that the used amounts of said raw materials satisfied $SiO_2$:$Al_2O_3$:tetrapropylammonium bromide:n-butylamine:water=100:0.67:4.5:35.3:300 (molar ratio), so as to prepare a composite ZSM-5 molecular sieve M10. The composite ZSM-5 molecular sieve had a length of 15 μm, a height of 4 μm, a width of 4 μm, and a specific surface area of 440 $m^2/g$.

The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Comparative Example 1

The molecular sieve was prepared according to the method of Example 1, except that the used amounts of said raw materials satisfied $SiO_2$:$Al_2O_3$:tetrapropylammonium bromide:n-butylamine:water=100:0.67:1.5:60:3,333 (molar ratio), so as to prepare a composite ZSM-5 molecular sieve D1.

Figure 6:
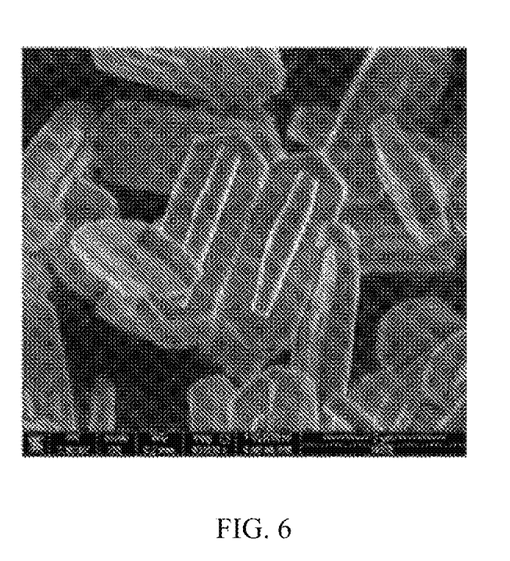
FIG. 6 illustrates a SEM diagram of the ZSM-5 molecular sieve obtained in Comparative Example 1.

The SEM spectrogram of the composite ZSM-5 molecular sieve D1 was shown in FIG. 6. The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Comparative Example 2

The molecular sieve was prepared according to the method of Example 1, except that the used amounts of said raw materials satisfied $SiO_2$:$Al_2O_3$:tetrapropylammonium bromide:n-butylamine:water=100:0.67:6:2:3,333 (molar ratio), so as to prepare a composite ZSM-5 molecular sieve D2.

Figure 7:
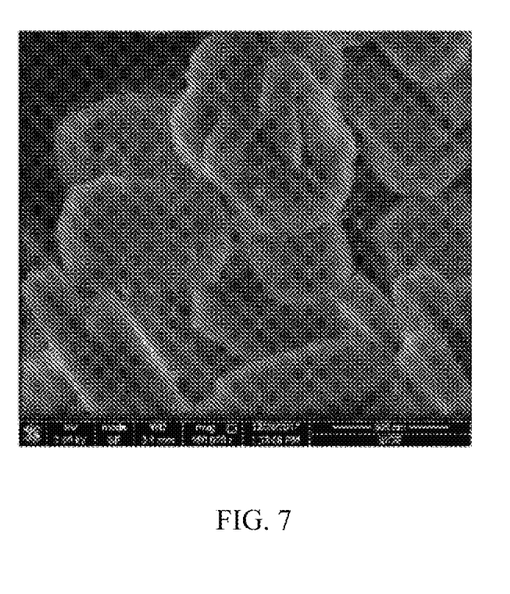
FIG. 7 illustrates a SEM diagram of the ZSM-5 molecular sieve obtained in Comparative Example 2.

The SEM spectrogram of the composite ZSM-5 molecular sieve D2 was shown in FIG. 7. The ratio of the number of sinusoidal pore openings to the number of straight pore openings on the external surface of the composite ZSM-5 molecular sieve, and the values of $Y_1$ and $Y_2$ of the composite ZSM-5 molecular sieve were shown in Table 1.

Comparative Example 3

The molecular sieve was prepared according to the method of Example 1, except that n-butylamine was replaced with an equivalent molar weight of tetrabutylammonium hydroxide to prepare the ZSM-5 molecular sieve D3.

The ratio of the number of sinusoidal pore openings to the number of straight pore openings on the external surface of the ZSM-5 molecular sieve, and the values of $Y_1$ and $Y_2$ of the composite ZSM-5 molecular sieve were shown in Table 1.

Comparative Example 4

The molecular sieve was prepared according to the method of Example 1, except that tetrapropylammonium bromide was replaced with an equivalent molar weight of ethanol amine to prepare the ZSM-5 molecular sieve D4.

The ratio of the number of sinusoidal pore openings to the number of straight pore openings on the external surface of the ZSM-5 molecular sieve, and the values of $Y_1$ and $Y_2$ of the composite ZSM-5 molecular sieve were shown in Table 1.

Comparative Example 5

The molecular sieve was prepared according to the method of Example 1, except that n-butylamine was replaced with an equivalent molar weight of triethylamine to prepare the ZSM-5 molecular sieve D5.

The ratio of the number of sinusoidal pore openings to the number of straight pore openings on the external surface of the ZSM-5 molecular sieve, and the values of $Y_1$ and $Y_2$ of the composite ZSM-5 molecular sieve were shown in Table 1.

Comparative Example 6

The molecular sieve was prepared according to the method of Example 1, except that n-butylamine was replaced with an equivalent molar weight of triethanolamine to prepare the ZSM-5 molecular sieve D6.

The ratio of the number of sinusoidal pore openings to the number of straight pore openings on the external surface of the ZSM-5 molecular sieve, and the values of $Y_1$ and $Y_2$ of the composite ZSM-5 molecular sieve were shown in Table 1.

Comparative Example 7

The molecular sieve was prepared according to the method of Example 2, except that the pH was adjusted to 13.8 to prepare the ZSM-5 molecular sieve D7.

The ratio of the number of sinusoidal pore openings to the number of straight pore openings on the external surface of the ZSM-5 molecular sieve, and the values of $Y_1$ and $Y_2$ of the composite ZSM-5 molecular sieve were shown in Table 1.

Example 11

The composite ZSM-5 molecular sieves M1-M10 and ZSM-5 molecular sieves D1-D7 prepared in the above Examples and Comparative Examples were used in the alkylation reaction of toluene methanol under the following reaction conditions: a reaction temperature of 470° C., a reaction pressure of atmospheric pressure, the reaction was carried out under a hydrogen atmosphere, a molar ratio of toluene to methanol in the liquid feedstock was 6:1, the feedstock was fed by a peristaltic pump, the feeding rate was 0.03 mL/min, and the used amount of said molecular sieve catalyst was 0.2 g.

The toluene conversion and p-xylene selectivity were calculated after the reaction was completed, the results were shown in Table 1.

Toluene conversion=(molar amount of toluene feed−molar amount of toluene discharge)/molar amount of toluene feed×100%;

P-xylene selectivity=molar amount of p-xylene discharge/(molar amount of p-xylene discharge+molar amount of m-xylene discharge+molar amount of o-xylene discharge)×10000.

TABLE 1

| | The ratio of the number of sinusoidal pore openings to the number of straight pore openings | $Y_1$ | $Y_2$ | Toluene conversion % | P-xylene selectivity % |
|---|---|---|---|---|---|
| Example 1 | 2.9 | 1000 | 150 | 10.4 | 99.4 |
| Example 2 | 2.6 | 980 | 150 | 10.5 | 98.6 |
| Example 3 | 1.7 | 930 | 140 | 11.0 | 97.3 |
| Example 4 | 1.4 | 930 | 130 | 10.3 | 97.1 |
| Example 5 | 1.3 | 870 | 125 | 7.8 | 95.1 |
| Example 6 | 1.2 | 710 | 120 | 8.3 | 90.3 |
| Example 7 | 1.5 | 610 | 140 | 9.2 | 82.2 |
| Example 8 | 1.0 | 530 | 154 | 8.0 | 84.4 |
| Example 9 | 1.8 | 500 | 136 | 10.1 | 87.5 |
| Example 10 | 0.9 | 630 | 135 | 9.1 | 81.4 |
| Comparative Example 1 | 0.8 | 150 | 147 | 11.1 | 79.5 |
| Comparative Example 2 | 0.6 | 130 | 134 | 11.4 | 73.6 |
| Comparative Example 3 | 0.8 | 125 | 125 | 12.7 | 78.2 |
| Comparative Example 4 | 0.7 | 148 | 150 | 12.9 | 60.3 |
| Comparative Example 5 | 0.4 | 120 | 145 | 15 | 34.0 |
| Comparative Example 6 | 0.4 | 130 | 150 | 16 | 24 |
| Comparative Example 7 | 0.4 | 138 | 150 | 16 | 24 |

As can be seen from the above Examples, Comparative Examples and results show in Table 1, a single crystal of the composite ZSM-5 molecular sieve comprises a main crystal and a twin crystal; wherein the main crystal and the twin crystal are both ZSM-5 crystals; a crystal plane [010] of the main crystal is covered by a crystal plane [100] of the twin crystal, such that the ratio of the number of sinusoidal pore openings to the number of straight pore openings on the external surface of the single crystal of the composite ZSM-5 molecular sieve is high, such as large than 0.8; in addition, as shown in data of the molar ratio $Y_1$ of Si element to Al element within 10 nm of the surface of the composite ZSM-5 molecular sieve and the molar ratio $Y_2$ of Si element to Al element of the composite ZSM-5 molecular sieve as a whole, the composite ZSM-5 molecular sieve of the present disclosure is aluminum-poor on the surface and aluminum-rich on the inside; as compared with the result data of the Comparative Examples 1-7, the composite ZSM-5 molecular sieve of the present disclosure is applied in the alkylation reaction of toluene methanol to prepare p-xylene, it can effectively improve the p-xylene selectivity in the alkylation reaction of toluene methanol to prepare p-xylene.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A composite ZSM-5 molecular sieve whose a single crystal comprises a main crystal and a twin crystal; wherein the main crystal and the twin crystal are both ZSM-5 crystals; a crystal plane [010] of the main crystal is covered by a crystal plane [100] of the twin crystal; the ratio of the number of sinusoidal pore openings to the number of straight pore openings on the external surface of the single crystal of the composite ZSM-5 molecular sieve is (0.7-10:1); the molar ratio $Y_1$ of Si element to Al element within 10 nm of the surface of the composite ZSM-5 molecular sieve is (300-2,000):1, wherein the composite ZSM-5 molecular sieve is prepared by mixing a silicon source and an aluminum source in the presence of water, a first templating agent and a second templating agent, wherein a molar ratio of the used amount of the silicon source, the aluminum source, the first templating agent, the second templating agent and water is 100:(0.08-2.5):(0.5-6):(0.5-60):(100-4,000), wherein the silicon source is calculated in terms of $SiO_2$, the aluminum source is calculated in terms of $Al_2O_3$.

2. The composite ZSM-5 molecular sieve of claim 1, wherein the ratio of the number of sinusoidal pore openings to the number of straight pore openings on the external surface of the single crystal of the composite ZSM-5 molecular sieve is (0.9-3.2):1.

3. The composite ZSM-5 molecular sieve of claim 1, wherein the molar ratio $Y_1$ of Si element to Al element within 10 nm of the surface of the composite ZSM-5 molecular sieve is (500-1,200):1.

4. The composite ZSM-5 molecular sieve of claim 1, wherein the molar ratio $Y_2$ of Si element to Al element of the composite ZSM-5 molecular sieve as a whole is (20-600):1.

5. The composite ZSM-5 molecular sieve of claim 4, wherein the molar ratio $Y_2$ of Si element to Al element of the composite ZSM-5 molecular sieve as a whole is (50-300):1.

6. The composite ZSM-5 molecular sieve of claim 1, wherein a single crystal of the composite ZSM-5 molecular sieve has a length of 10-50 μm, a height of 1-20 μm and a width of 1-20 μm; and a single crystal of the composite ZSM-5 molecular sieve has a specific surface area of 200-600 m²/g.

7. A catalyst comprising the composite ZSM-5 molecular sieve of claim 1.

8. A method of using the composite ZSM-5 molecular sieve of claim 1 in the alkylation reaction of toluene methanol to prepare p-xylene.

9. The composite ZSM-5 molecular sieve of claim 1, wherein p-xylene selectivity of the composite ZSM-5 molecular sieve in alkylation reaction of toluene is 81.4% or more.

10. A method for preparing a composite ZSM-5 molecular sieve comprising:
(1) mixing a silicon source and an aluminum source in the presence of water, a first templating agent and a second templating agent, adjusting the pH to be within a range of 11-13.5, and then performing crystallization;
(2) subjecting the crystallized product to a solid-liquid separation, and calcining the obtained solid phase to prepare the composite ZSM-5 molecular sieve;
wherein the first templating agent is at least one selected from the group consisting of tetraethylammonium hydroxide, tetrapropylammonium hydroxide, tetrapropylammonium bromide and tetrabutylammonium hydroxide, the second templating agent is at least one selected from the group consisting of ethylenediamine, n-butylamine, hexamethylenediamine, ethylamine, ethanol and ethanolamine; and the used amount of the first templating agent to the second templating agent in a molar ratio is 1:(1-30),
wherein a molar ratio of the used amount of the silicon source, the aluminum source, the first templating agent, the second templating agent and water is 100:(0.08-2.5):(0.5-6):(0.5-60):(100-4,000); wherein the silicon source is calculated in terms of $SiO_2$, the aluminum source is calculated in terms of $Al_2O_3$.

11. The method of claim 10, wherein a molar ratio of the used amount of the first templating agent to the second templating agent is 1:(3-20).

12. The method of claim 10, wherein the pH in step (1) is adjusted to 11.2-13.

13. The method of claim 10, wherein the crystallization conditions in step (1) comprise a temperature of 120-250° C. and a time of 12-72 h;
the calcination conditions in step (2) comprise a temperature of 500-700° C., and a time of 1-24 h.

14. The method of claim 13, wherein the crystallization conditions in step (1) comprise a temperature of 150-180° C. and a time of 24-60 h;
the calcination conditions in step (2) comprise a temperature of 500-700° C., and a time of 4-12 h.

15. The method of claim 10, wherein the solid phase obtained from the solid-liquid separation is subjected to drying prior to calcining.

16. The method of claim 15, wherein the drying conditions comprise a temperature of 90-200° C. and a time of 2-12 h.

17. The composite ZSM-5 molecular sieve produced with the preparation method of claim 10.

18. The method of claim 10, wherein a molar ratio of the used amount of the silicon source, the aluminum source, the first templating agent, the second templating agent and water is 100:(0.4-2):(1-6):(3-30):(500-4,000).

* * * * *